Figure 2:
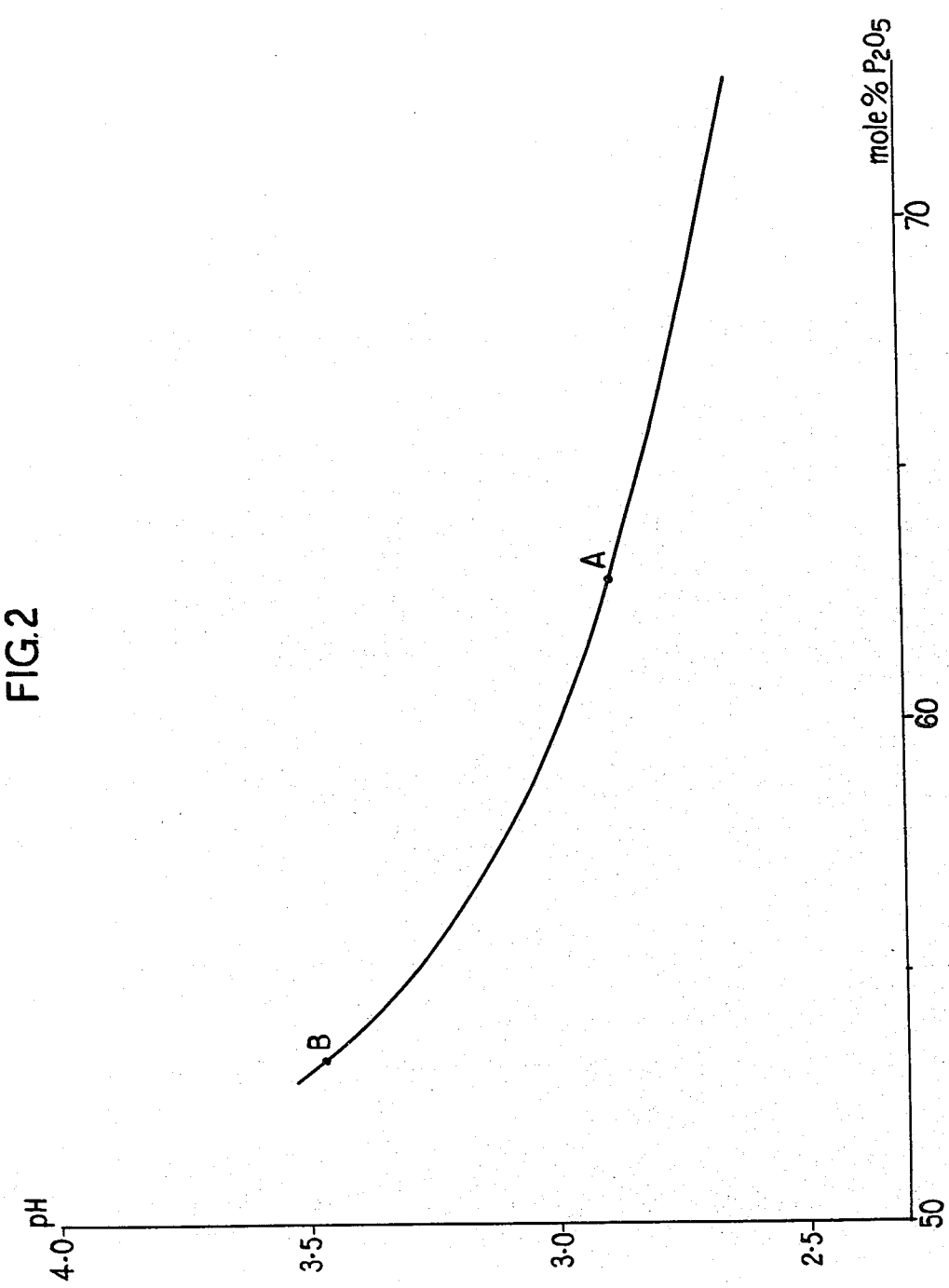

United States Patent [19]

Drake

[11] 4,350,675

[45] Sep. 21, 1982

[54] CONTROLLED RELEASE GLASS

[75] Inventor: Cyril F. Drake, Harlow, England

[73] Assignee: International Standard Electric Corporation, New York, N.Y.

[21] Appl. No.: 180,068

[22] Filed: Aug. 21, 1980

[30] Foreign Application Priority Data

Aug. 30, 1979 [GB] United Kingdom ............... 7930041

[51] Int. Cl.³ ................. A61K 49/00; A61K 43/00; A45C 13/10

[52] U.S. Cl. ..................... 424/1; 71/64.11; 71/904; 424/1.5; 424/9; 501/11

[58] Field of Search ................ 106/47 R; 424/1, 1.5, 424/9; 71/64 F, 64 G

[56] References Cited

U.S. PATENT DOCUMENTS

| | | | |
|---|---|---|---|
| 3,930,833 | 1/1976 | Roberts | 71/64 G |
| 3,958,973 | 5/1976 | Roberts | 71/64 G |
| 4,052,010 | 10/1977 | Baker et al. | 424/1.5 |
| 4,123,248 | 10/1978 | Drake | 71/64 G |
| 4,148,623 | 4/1979 | Drake | 71/64 F |
| 4,182,750 | 1/1980 | Sullivan et al. | 424/1 |
| 4,247,406 | 1/1981 | Widdeo et al. | 424/1 |
| 4,297,337 | 10/1981 | Mansfield et al. | 424/1.5 |
| 4,310,506 | 1/1982 | Baldeschwieler et al. | 424/1 |

Primary Examiner—Christine M. Nucker
Attorney, Agent, or Firm—James B. Raden; Harold J. Holt

[57] ABSTRACT

A controlled release glass is based on phosphorus pentoxide as the glass forming oxide and an alkali metal oxide as the principal glass modifier. The glass contains a modifying oxide of a material to be released slowly, e.g. one of the oxides of the alkali metal, or an oxide of an alkaline earth metal, an oxide of a metal of Group IIIA of the Periodic Table or a transition metal oxide, depending on the deficiency to be cured.

20 Claims, 4 Drawing Figures

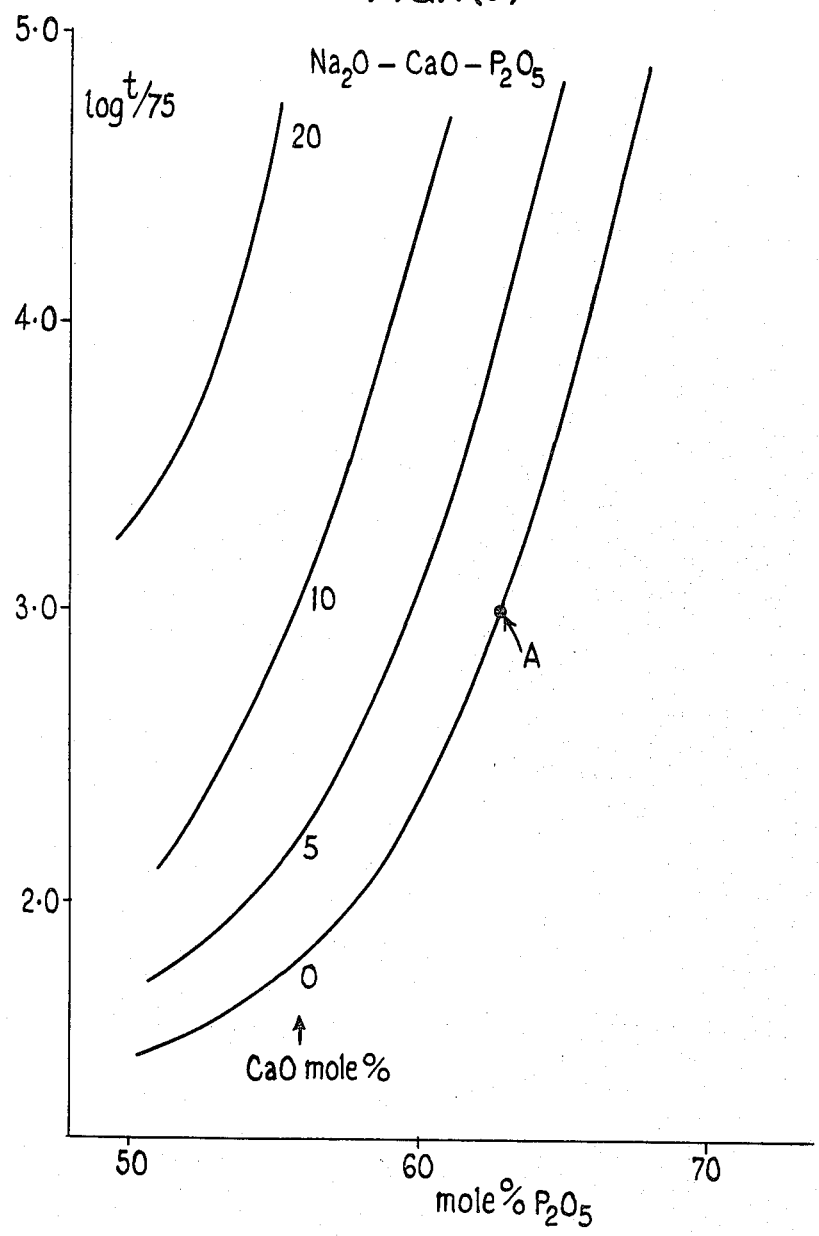

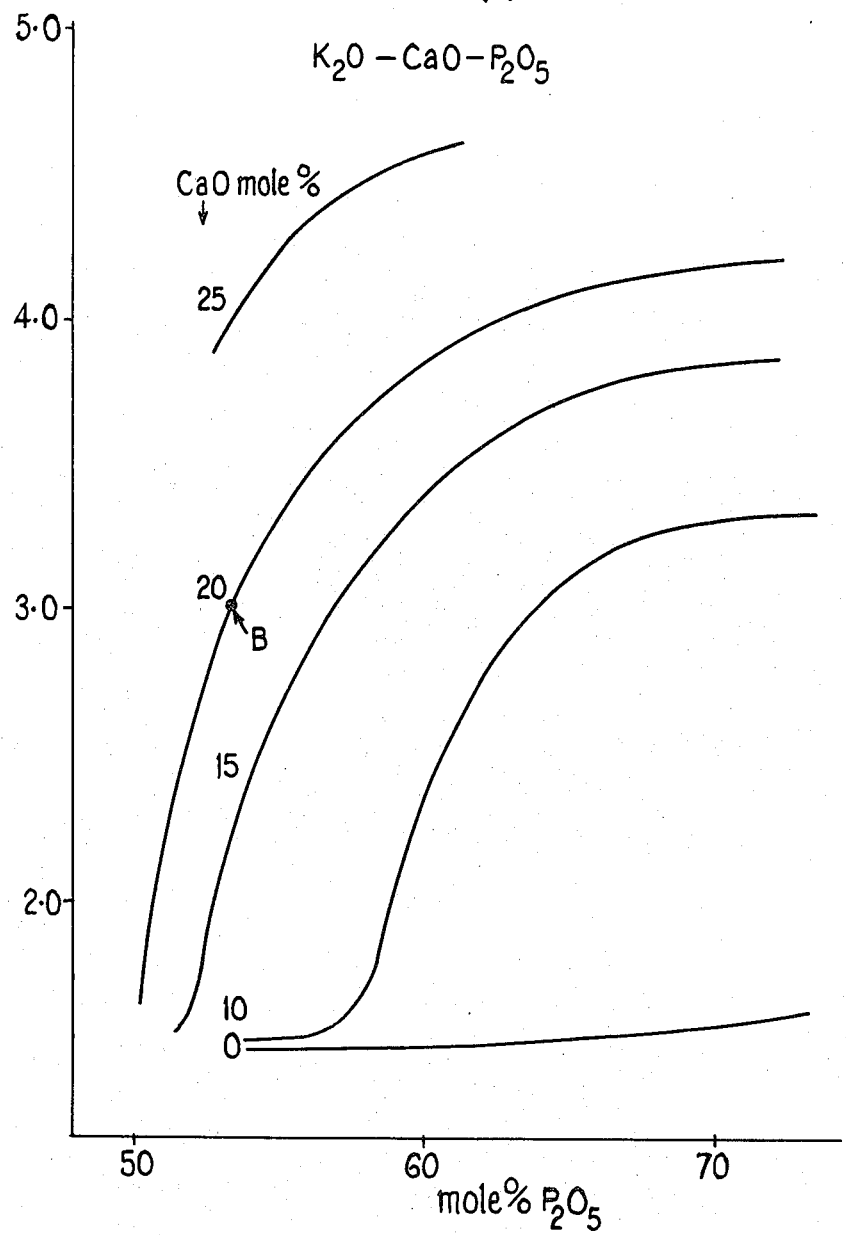

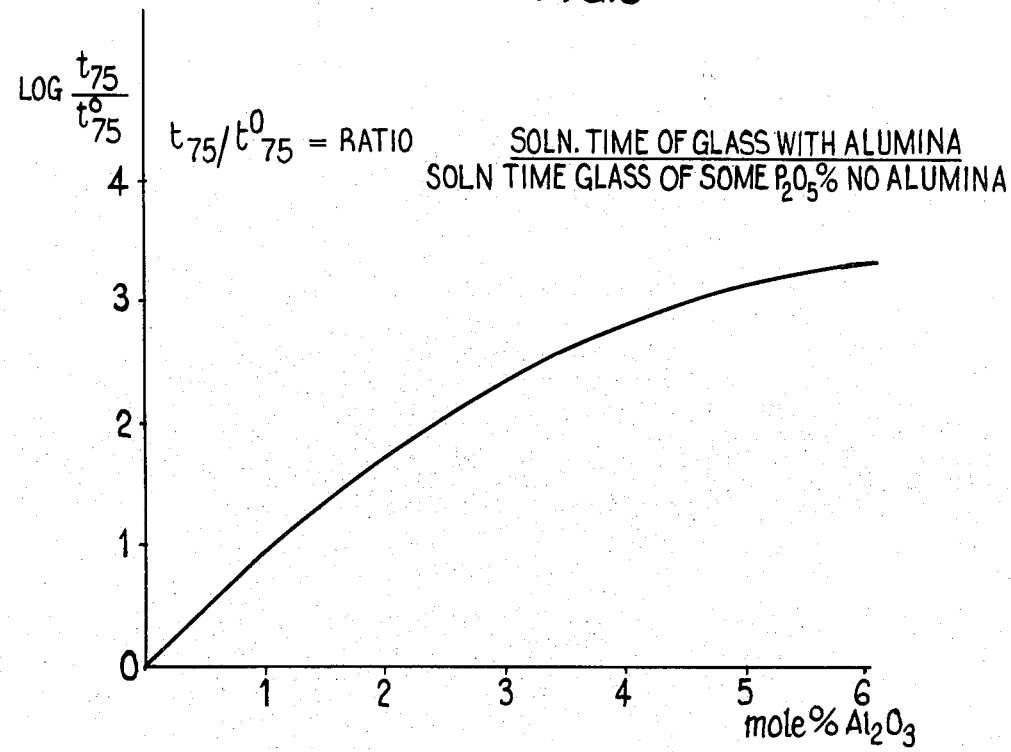

CONTROLLED RELEASE GLASS

This invention relates to glass compositions, and in particular to such compositions which are soluble in water or other polar solvents.

There are many circumstances in which it is useful to be able to produce a material which will dissolve in water at a predetermined rate. The use of stoichiometric compounds in such applications is limited by the fact that only a limited number of such compounds exist and, in a given chemical system, it is not possible to prepare compounds with a preselected rate of solution; at best a few rates, corresponding to the distinct compounds that exist, will be available.

According to one aspect of the invention there is provided a water soluble glass, comprising phosphorus pentoxide as the glass forming oxide, and one or more glass modifying oxides, the composition of the glass being selected from the composition/property charts of FIG. 1, FIG. 2, or FIG. 3, or any combination thereof.

According to another aspect of the invention there is provided a process for liberating a predetermined quantity of one or more metals into aqueous solution, including forming a glass being a composite selected from the composition/property charts of FIG. 1, FIG. 2, or FIG. 3 or any combination thereof and contacting the glass with water or an aqueous medium.

According to still another aspect of this invention there is provided a water soluble glass composition comprising from 50–75 mole percent of phosphorus pentoxide as the glass forming oxide, from 1–20 mole percent of an alkali metal oxide as the principal glass modifier, the remainder including from 1 to 25 mole percent of an oxide selected from the group consisting of alkaline earth metal oxides, an oxide of a metal of Group IIIA of the Periodic Table, a transition metal oxide and combinations of the foregoing, the aqueous solution time of said glass composition being controlled by adjusting the mole proportions of said oxides between the indicated ranges.

The graphs of FIGS. 1, 2, and 3, express the teaching of this invention in the following ways.

In FIGS. 1(a) and (b) the vertical axis is a practical parameter proportional to the reciprocal of the absolute solution rate (quantity of glass dissolved in deionised water per unit area of glass per unit time at 30° C.). It is the logarithm of the time in mins. required to dissolve 75% of a glass sample consisting of a 0.1 g of ground glass with a particle size between 500 and 710 pe and having a specific surface area of about $4° cm^2 g^{-1}$ which is shaken with 200 ml of deionized water at 30° C. This parameter is henceforth termed the solution time: $t_{75}$.

In FIG. 2 the vertical axis is the pH at 30° C. ultimately reached when 0.1 g of the specified glass has completely dissolved in 200 ml of deionized water.

FIG. 3 describes the effect on the solution rate of any of the glasses of the inclusion of $Al_2O_3$ in the glass. The vertical axis expresses the logarithm of the ratio of the solution time of any glass containing the specified mole % of $Al_2O_3$ to the solution rate of the equivalent glass containing no $Al_2O_3$ but the same mole % of $P_2O_5$ and CaO.

The applications of materials with a controlled and pre-selected solution rate can be described under three main headings:

(i) the use of such materials as 'timers' in aqueous solution;

(ii) the use of such materials as a means of releasing their major constituents at a controlled rate into an aqueous environment;

(iii) the use of such materials as a host material for a much smaller quantity of material incorporated therein.

In case (i) it will be shown to be possible to produce a material which will dissolve at a constant rate in an unchanging aqueous environment and hence will measure lapsed time after the material was brought in contact with the liquid. Alternatively, the fact that the solution rate is a function of, for example, the pH and temperature of the aqueous environment, makes possible the measurement of $$\int_0^t (pH)dt, \quad \int_0^t g(T)dt, \quad \text{or} \quad \int_0^t f(pH), g(T)dt,$$

where t is time and T temperature. Thus, if the functional dependence of solution rate on temperature is the same or nearly the same as that of a chemical reaction or of a biochemical process, then the course of this reaction or process can be followed by the extent of solution of the monitor material. Of course, the end point or 'danger point' of the reaction or process can be indicated by arranging that an indication will appear when the monitor material has dissolved to a certain predetermined degree.

Case (ii) can be illustrated by the facility it provides to release sodium and/or potassium ions at an accurately controlled rate into, for example, the human alimentary canal or into a saline or glucose drip used in medicine and as an adjunct to surgery. It is well known that the sodium/potassium ion balance must be accurately maintained in living organisms and any deviation must be corrected by medical intervention. For example, many patients on diuretics must take potassium containing pills but it is important that these should not release their total potassium content into the alimentary canal suddenly. The provision of a controlled-release potassium-based material which will steadily release its potassium during the time it takes to pass through the patient will clearly avoid this danger. A material of a similar type designed to release sodium and potassium in the correct ratio at the required rate can clearly be used in-line in a drip feed or intravenous solution to provide the required ions without periodic intervention and the consequent increased risk of infection. The glass composition may also be added to an aqueous nutrient medium for the culture of bacteria, fungi or other microbiological entities, and which when added will release nutrient ions at a predetermined rate and supply the culture with the optimum amount of one or more nutrient ions. The glass may also be added or inserted in line with the feed water for a fish farms tank or container.

In some cases it is required slowly to neutralize an alkali which is present initially or developed continuously in an aqueous system. A glass selected from FIG. 1 to provide the appropriate solution rate and according to FIG. 3 to yield the required amount of hydrogen ions is added to the said aqueous system.

Case (iii) can be illustrated by reference to a similar example to that in the previous paragraph. It is known that hospital patients on drip feed for extended periods must be supplied with very small quantities of trace elements such as zinc and copper. This provision of micro-quantities of the trace elements in accurately controlled amounts is at present very difficult. It requires the use of much skilled labor in the chemical laboratory to prepare the dose; such small quantities cannot be stored as they are readily precipitated or absorbed on the container walls; skilled medical staff must supervise the injection of the dose into the drip feed; and 'breaking' the sealed drip-feed system to administer them increases the risk of infection. From the previous example it will be clear that the very small quantities of these trace elements could be incorporated in the host material used for the release of sodium and/or potassium and would be released, together with the alkali metal, in the same proportions as those in which they are present in the controlled release materials. As another example we may take the case when it is desirable to release a radioactive atom, or 'tag' isotope, at a controlled rate into an aqueous system. In this case, as in all the preceding examples, it may be desirable to provide a release/time profile which is not constant. For example, it may be desirable that the rate of release should increase or decrease with time or even that there should be a pulsating release with periods of rapid release succeeded by intervals of very slow release. Such cases can be realized by a body which consists of, for example, concentric or parallel layers of the same basic material but with the layers formulated to have different solution rates.

Embodiments of the invention will now be described with reference to the drawings referred to above, in which FIGS. 1, 2 and 3 illustrate the relationship between the solution-rate of the glass and glass composition.

The main constituents of the glass materials are one or more than one of the alkali metal oxides and phosphorus pentoxide. In addition, one or more alkaline earth metal oxides or oxides of elements of Group IIIA may be present as a means of controlling the solution rate. Other oxides may be present as minor constituents in total quantity less than 10 mole %.

The anionic part of the material may also comprise small proportions of for example borate, silicate, germanate, sulphate or halide anions making up in total not more than 10% of the total anionic constituents.

The constituents are premixed and melted together at a temperature which will normally be between 700° C. and 1200° C. to form a homogeneous melt which produces a glass when cooled to room temperature. It will be obvious to those skilled in the art of glass making that batch materials other than oxides, i.e. oxide precursors, may be used without altering the properties of the resultant glass. For example, some or all of the metal oxides may be replaced be equimolar amounts of the carbonates or by hydroxides of the respective metal.

The homogeneous glass-forming melt described above can now be converted to the final product in a number of different ways. The particular process will be selected according to the requirements of the particular application. For example, glass rods can be drawn from the melt and subsequently cut into suitable lengths for insertion in-line into a drip-feed as described above. Alternatively, the glass can be drawn from the melt in the form of glass tubes which can be used to convey an aqueous liquid and, at the same time, to release the constituent ions into the liquid at a predetermined rate. In another example the glass is cast in the form of a thin sheet which is subsequently broken up, ground, and sieved to separate fractions of given particle size and, therefore, a given surface area per unit weight. This material can be fed as a dietary supplement to farm animals and will dissolve at a preselected rate as it passes through the animal's digestive system. Yet again, the glass can be cast into moulds to produce small discs which can be used in chemical timer systems as described in outline above.

The details of the methods to be used economically to produce a glass in any of the forms in the above examples, or in forms appropriate for other applications, for example as glass fibre, will be obvious to those skilled in the art of glass-working. It will also be obvious in some cases, for example when the final product is a monolithic block of, for example, animal lick, that the glass will need to be annealed in order to prevent it shattering when cooled and again, the temperature-time cycle for such an anneal will be obvious to those skilled in the art.

The crucible in which the glass is melted can be selected from materials which will not be destroyed by the temperature necessary for melting nor by the phosphate melts. Platinum and platinum-alloy crucibles of the types commercially available have been found to be entirely suitable for preparing these glasses. However, in some cases it may be desirable to use cheaper materials for the glass melting. A crucible material that is commonly used in pure alumina or stabilized alumina and it is important if such a material is used that precautions be taken, for example by cooling the crucible wall, to prevent the glass product being contaminated by $Al_2O_3$ dissolved from the crucible. The effect of very small quantities of $Al_2O_3$, i.e. not more than 5 mole % on the rate of solution of phosphate-based glasses in aqueous solutions has not hitherto been appreciated, with the exception of the special case of a $Na_2O:P_2O_5:M_2O_3$ glass containing between 46 and 50 mole % of $P_2O_5$ disclosed in U.S. Pat. No. 3,272,588. We have found that the concentration of $Al_2O_3$, in the glass product must be accurately controlled, and that, to produce a glass with a predetermined solution rate, the various constituents, including the $Al_2O_3$, must be present in the glass materials in predetermined proportions.

The glasses comprise $P_2O_5$ as the principal glass former and one or more alkali metal oxide or oxides as the principal glass modifier, the proportions of these constituents being selected according to the graphs and tables included herein. The glasses may consist of the glass-former $P_2O_5$ and one or more alkali metal oxides only or they may contain a minor proportion of an alkaline earth metal oxide or an oxide of a metal of Group IIIA of the Periodic Table. The preferred alkaline earth metal ozide is CaO and the preferred Group IIIA metal oxide is $Al_2O_3$ and the proportion of these is selected according to the graphs and tables included herein. It will be understood that a part of the whole of the CaO can be replaced by other alkaline earth metal oxides but that in this case the exact proportions required to obtain a predetermined solution rate will have to be adjusted accordingly. Similarly, it has been found that $Ga_2O_3$, for example, may replace part or the whole of the $Al_2O_3$. Another trivalent metal oxide that has been found to be a suitable replacement for $Al_2O_3$ is a metal sesquioxide such as $Fe_2O_3$ which is not, of course, a member of the Group IIIA of the Periodic Table. The glasses with their major constituents, and minor constituents if present, may also contain minor amounts of other metal oxides which do not significantly change the solution rates of the glass. These metal oxides comprise, for example, one or more transition metal oxides which are released into solution as the glass dissolves in the same proportions relative to the total mass of the glass dissolved as that in which they are present in the original glass.

Another feature of the glass composition is the facility to predetermine independently both the pH of the solution produced when the glass dissolves and the rate at which it dissolves. For example, by reference to FIG. 1 and FIG. 2 it will be clear that if it is known that a solution time of 1000 min is required it can be obtained by selecting a glass of composition A which will give a pH of 2.78 or by selecting glass B giving a pH of 3.47. It is also possible to produce a timer for processes occurring in or in contact with, an aqueous medium by combining a suitably shaped specimen of the glass material with means to determine the amount of the specimen that has been dissolved at any given time or with means to determine the time at which all or a preselected proportion of the specimen has been dissolved.

Another feature of the glass composition is related to the form of the phosphate anion as it is first released from the glassy network into the aqueous phase. By the nature of the phosphate phase we mean the relative proportions of the total phosphorus in solution which is present as ortho-phosphate ($PO_4^{3-}$), pyrophosphate ($P_2O_7^{4-}$), various polyphosphates, including chain and ring polyphosphates. It will be understood that we refer here to the phosphorus in the form it is present immediately after it has been released into the solution from the glass network. It is well known that all the phosphate forms tend to be hydrolyzed in solution to give the orthophosphate ion as the ultimate product. In a number of applications of the glasses which are the subject of this invention, the form of the phosphorus is of importance. It is well known that many cations form complexes with pyro and more complex phosphates and that the stability constant of these complexes is high enough for the cation not to be precipitated in the presence of concentrations of $OH^-$ of $CO_3^{2-}$ ions which would normally produce said precipitation. Thus, the facility simultaneously to release a cation contained as a minor constituent of an alkali metal phosphate glass and the phosphate as a polyphosphate can prevent the precipitation of an insoluble hydroxide, carbonate, or basic carbonate of said cation when it is released in natural aqueous solutions in which the pH is so high or the $CO_2$ content is high that in the absence of the polyphosphate it would be precipitated.

To summarize, glass forming oxides usable include $Si_2O_3$, $B_2O_3$, $GeO_2$, $As_2O_3$ or $Sb_2O_5$, and materials using the group $SO_4$: these can replace up to 10% of the $P_2O_5$.

Materials to be dispersed from the glass include ones with the ions $Li^+$, $Na^+$, $K^+$, $Cs^+$, $Rb^+$, $PO_4^{3-}$, $Ca^{3+}$ and $Al^{3+}$. Other suitable materials include Cu, Zn, Mg, Co and Mn.

I claim:

1. A process of dispersing a predetermined quantity of at least one metal into an aqueous medium in man, animal or a microbiological entity comprising
    contacting an aqueous medium in man, animal or a microbiological entity with a water soluble glass composition consisting essentially of from 50-75 mole percent of phosphorus pentoxide as the glass forming oxide; from 1-20 mole percent of an alkali metal oxide as the principal glass modifier, the remainder including from 1-25 mole percent of an oxide selected from the group consisting of an alkaline earth metal oxide, an oxide of a metal of Group IIIA of the Periodic Table, a transition metal oxide and combinations of the foregoing, the aqueous solution time of said glass composition being controlled by adjusting the mole proportions of said oxides between the indicated ranges.

2. The process of claim 1 in which the glass composition is taken orally by man or animal and the metal is released in the form of its ion into the alimentary canal at a predetermined rate.

3. The process of claim 1 in which a portion, not exceeding 10 mole percent of the phosphorus pentoxide, is replaced by another glass-forming oxide selected from the group consisting of $SiO_3$, $B_2O_3$, $GeO_2$, $As_2O_3$, $Sb_2O_3$ and an oxide containing the group $SO_4$.

4. The process of claim 1 in which the principal glass modifier is selected from the group consisting of sodium and potassium oxide.

5. The process of claim 1 containing an alkaline earth metal oxide.

6. The process of claim 5 in which the alkaline earth metal oxide is calcium oxide.

7. The process of claim 1 in which the glass composition contains up to 10% of a metal sesquioxide $M_2O_3$.

8. The process of claim 7 in which the metal sesquioxide is $Fe_2O_3$.

9. The process of claim 1 in which the glass composition contains a Group IIIA metal oxide.

10. The process of claim 1 in which the glass composition contains up to 6% $Al_2O_3$.

11. The process of claim 1 in which at least one inorganic ion is dispersed from the glass composition, the ion being selected from the group consisting of $Li^+$, $Na^+$, $K^+$, $Cs^+$, $Rb^+$, $PO_4^{3-}$, (polyphosphate) $^{n-}$, $Ca^{2+}$ AND $Al^{3+}$.

12. The process of claim 1 in which inorganic ions are dispersed from the glass composition, the ions including a tagged ion such as a radioactive isotope.

13. The process of claim 1 in which farm or ranch animals are supplied with supplementary minerals by dispersing said metal from a monolithic block of animal lick made from said glass composition.

14. The process of claim 13 in which the mineral supplement includes an ion selected from the group consisting of sulphate and phosphate and an oxide selected from the group consisting of $Na^+$, $K^+$, $Ca^{++}$ and $Mg^{++}$.

15. The process of claim 13 in which the mineral supplement includes at least one element selected from the group consisting of Cu, Zn, Mg, Co and Mn.

16. The process of claim 1 in which mineral ion supplements are dispersed by feeding into a saline, glucose, or other drip-feed by inserting said glass composition into the drip-feed.

17. The process of claim 16 in which the minerals are selected from the group consisting of Na and K.

18. The process of claim 1 in which the glass composition is added to an aqueous system to produce hydrogen ions at a predetermined rate to neutralize at a predetermined rate alkali initially present or subsequently developed in the system.

19. The process of claim 1 in which the glass composition is added to an aqueous nutrient medium for the culture of bacteria, fungi or other microbiological entities, said aqueous nutrient medium releasing nutrient ions at a predetermined rate to supply the culture with the optimum amount of one or more nutrient ions.

20. The process of claim 1 in which the glass composition is added to or inserted in-line with the feed water for a fish farms tank or container.

* * * * *